(12) United States Patent
Chen et al.

(10) Patent No.: US 8,835,445 B2
(45) Date of Patent: Sep. 16, 2014

(54) DIHYDROFOLATE REDUCTASE INHIBITORS

(75) Inventors: Zhiyong Chen, San Diego, CA (US); Christopher J. Creighton, San Diego, CA (US); Mark Cunningham, San Diego, CA (US); John Finn, San Diego, CA (US); Mark Hilgers, San Diego, CA (US); Michael Jung, Los Angeles, CA (US); Lucy Aguirre Kohnen, Cambridge, MA (US); Thanh Lam, San Diego, CA (US); Xiaoming Li, San Diego, CA (US); Mark Stidham, San Diego, CA (US); Les Tari, San Diego, CA (US); Michael Trzoss, San Diego, CA (US); Junhu Zhang, San Diego, CA (US)

(73) Assignee: Trius Therapeutics, Inc., San Diego, CA (US)

( * ) Notice: Subject to any disclaimer, the term of this patent is extended or adjusted under 35 U.S.C. 154(b) by 73 days.

(21) Appl. No.: 13/151,683

(22) Filed: Jun. 2, 2011

(65) Prior Publication Data

US 2012/0136014 A1 May 31, 2012

Related U.S. Application Data

(60) Provisional application No. 61/350,886, filed on Jun. 2, 2010.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ............... 514/266.1; 514/266.2; 544/283; 544/284

(58) Field of Classification Search
USPC ............ 544/283, 284; 540/484; 514/266.1, 514/266.2
See application file for complete search history.

(56) References Cited

U.S. PATENT DOCUMENTS

| | | | |
|---|---|---|---|
| 5,534,518 A | 7/1996 | Henrie et al. | |
| 7,678,803 B2 * | 3/2010 | Huang et al. | 514/266.2 |
| 2004/0229890 A1 | 11/2004 | Berthel et al. | |
| 2006/0211715 A1 | 9/2006 | Berthel et al. | |
| 2008/0070935 A1 * | 3/2008 | Huang et al. | 514/264.11 |
| 2009/0118311 A1 | 5/2009 | Davidson | |
| 2009/0312305 A1 | 12/2009 | Beard et al. | |

FOREIGN PATENT DOCUMENTS

| | | |
|---|---|---|
| WO | WO 94/18980 | 9/1994 |
| WO | WO 2006/050843 | 5/2006 |

OTHER PUBLICATIONS

Vippagunta et al.*
Finn et al. Structure-Based Design of New DHFR-based Antibacterial Agents (Part 2): (Benzimidazol-1-yl)-2,4-diaminoquinazolines SAR, retrieved from http://www.triusrx.com/pdfs/Structure-Based-Design-of-New-DHFR-Antibacterial-Agents(Part%202).pdf (on Apr. 5, 2012).
Rosowsky and Papathanasopoulos "Quinazolines. XIII. Synthesis of Polycyclic 2,4-Diaminopyrimidines from Aromatic Amine Hydrochlorides and Sodium Dicyanamide1,2," J. Org. Chem., 39(22): 3293-5 (1974).
Cikotiene and Morkunas, "The First and Efficient Synthesis of 7-Aryl-6-methoxycarbonylquinazolines via Unexpected Reaction of 6-Arylethynylpyrimidine-5-carbaldehydes and Methyl Mercaptoacetate," Synlett (2): 284-286 (2009).
Chemical Abstracts Service, Columbus Ohio, US: CAS Registry No. 1027917-45-8 (Jun. 1, 2011); CAS Registry No. 1137439-84-9 (Jun. 1, 2011); CAS Registry No. 159018-81-2 (Jun. 1, 2011); CAS Registry No. 180268-99-9 (Jun. 1, 2011); CAS Registry No. 52306-21-5 (Jun. 1, 2011); CAS Registry No. 887232-80-6 (Jun. 1, 2011); CAS Registry No. 887232-82-8 (Jun. 1, 2011); CAS Registry No. 887232-91-9 (Jun. 1, 2011); CAS Registry No. 887232-96-4 (Jun. 1, 2011); CAS Registry No. 887233-15-0 (Jun. 1, 2011); CAS Registry No. 887233-17-2 (Jun. 1, 2011); CAS Registry No. 887233-19-4 (Jun. 1, 2011); CAS Registry No. 887233-21-8 (Jun. 1, 2011); CAS Registry No. 887233-26-3 (Jun. 1, 2011); CAS Registry No. 887233-28-5 (Jun. 1, 2011).

* cited by examiner

*Primary Examiner* — Paul V. Ward
(74) *Attorney, Agent, or Firm* — DLA Piper LLP (US)

(57) ABSTRACT

The present disclosure provides compounds of Formula I:

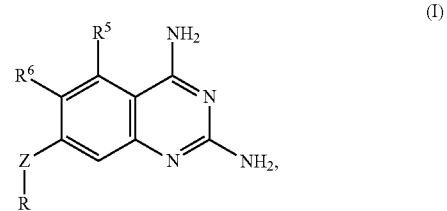

or a pharmaceutically acceptable salt thereof, wherein $R^5$, $R^6$ and Z are as described herein. The disclosure also provides pharmaceutical compositions thereof; and methods for inhibiting DHFR activity; and methods for treating cell proliferative diseases, autoimmune disease, inflammatory disease or bacterial, fungal or parasitic infection by administering a compound of Formula I.

15 Claims, No Drawings

DIHYDROFOLATE REDUCTASE INHIBITORS

CROSS REFERENCE TO RELATED APPLICATIONS

This application claims the benefit of priority under 35 U.S.C. §119(e) to U.S. Provisional Application No. 61/350,886 filed on Jun. 2, 2010, the disclosure of which is hereby incorporated by reference in their entirety for all purposes.

FIELD OF THE INVENTION

The disclosure relates to compounds and compositions that inhibit the dihydrofolate reductase (DHFR) family of enzymes; methods of making and using these compounds and compositions for the treatment and prophylaxis of diseases in mammals including the treatment of cell proliferative diseases such as cancers and inflammation, and to their use as anti-infective agents for bacterial, fungal or parasitic infection.

BACKGROUND OF THE INVENTION

Bacterial infections pose a continuing medical problem because anti-bacterial drugs eventually engender resistance in the bacteria on which they are used. Consequently, a need exists for new drugs with efficacy against pathogenic bacteria for use in the therapy and prophylaxis of bacterial infections.

One target for development of anti-bacterial drugs has been dihydrofolate reductase (DHFR), an enzyme on the synthetic pathway to purine and pyrimidine nucleotides. DHFR inhibitors have been disclosed in US 20090118311, which is hereby incorporated by reference in its entirety.

Folate (pteroylglutamate) is a vitamin which is a key component in the biosynthesis of purine and pyrimidine nucleotides. Following absorption, dietary folate is reduced to dihydrofolate and then further reduced to tetrahydrofolate by the enzyme dihydrofolate reductase (DHFR). Inhibition of DHFR leads to a reduction in nucleotide biosynthesis resulting in inhibition of DNA biosynthesis and reduced cell division. DHFR inhibitors are widely used in the treatment of cancer, cell proliferative diseases such as rheumatoid arthritis, psoriasis and transplant rejection. DHFR inhibitors have also found use as anti-infective and anti-parasitic agents. Many types of DHFR inhibitor compounds have been suggested, and several such compounds are used as anti-cancer, anti-inflammatory, anti-infective and anti-parasitic agents.

Methotrexate is the most widely used DHFR inhibitor, which contains a glutamate functionality that enables it to be actively transported into and retained inside of cells. However, cancer cells can become resistant to methotrexate by modifying this active transport mechanism. Furthermore, non-mammalian cells lack the active transport system and methotrexate has limited utility as an anti-infective agent. Lipophilic DHFR inhibitors which can be taken up by passive diffusion into cells have therefore been developed both to circumvent cancer cell resistance and for use as anti-infective agents. However, agents that passively diffuse into cells also exit the cell readily. Thus, there remains a need in the art for DHFR inhibitors that accumulate in cells in a way that does not depend on the active transport mechanism of methotrexate or on the lipophilicities.

SUMMARY OF THE INVENTION

The disclosure addresses these needs by providing new compounds and pharmaceutical compositions thereof, for inhibiting DHFR activity and for treating cell proliferative diseases, autoimmune diseases, inflammatory diseases or bacterial, fungal or parasitic infections. Thus, in one embodiment the disclosure provides compounds of Formula I

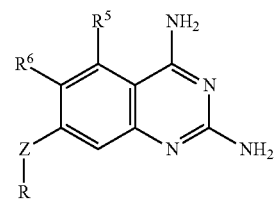

Formula I wherein:

Z is a five to 10-membered aryl or heteroaryl ring compound comprising 0-4 heteroatoms independently selected from the group consisting of N, O, and S;

R represents one or more moieties independently selected from the group consisting of H, halo, lower alkyl, lower alkoxy, CF3, amino, CN, and optionally-substituted aryl, and optionally-substituted heterocyclyl;

$R^5$ is selected from the group consisting of H, halo, lower alkyl, and lower alkoxy;

$R^6$ is selected from the group consisting of H, halo, lower alkyl, lower alkoxy, CF3, 5-membered heteroarylmethylene, and amino; and pharmaceutically acceptable salts, solvates, and prodrugs thereof.

The disclosure also provides pharmaceutical compositions of the compound of Formula I, and methods for inhibiting DHFR activity and for treating cell proliferative diseases, autoimmune diseases, inflammatory diseases or bacterial, fungal or parasitic infections using the compound of Formula I.

DETAILED DESCRIPTION OF THE INVENTION

Unless otherwise specified, technical terms take the meanings specified in the McGraw-Hill Dictionary of Scientific and Technical Terms, 6th edition.

Definitions

"Alkyl" refers to substituents derived from optionally-substituted saturated hydrocarbons, whether cyclic or acyclic, by removal of one or more hydrogen atoms.

"Lower alkyl" refers to optionally-substituted acyclic alkyl groups having one to six carbon atoms, and to cyclic alkyl groups having three to six carbon atoms.

Similarly, "lower alkoxy" refers to —OR groups where R comprises a chain of one to six carbon atoms.

"Aryl" refers to optionally-substituted monocyclic and fused bicyclic carbocyclic groups having from five to 12 carbon atoms and having at least one aromatic ring. Examples of particular aryl groups include phenyl and naphthyl.

"Heterocyclic," "heterocycle," and "heterocyclyl" refer to optionally-substituted monocyclic and fused bicyclic groups, saturated or unsaturated, aromatic or non-aromatic, having the specified number of members and including 1-4 heteroatoms selected from N, O and S. Examples include tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, and tetrahydrothiophene.

"Heteroaryl" refers to those heterocycles defined above that are aromatic. Examples of particular heteroaryl groups include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole.

The term "members" or "membered" in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

"Optionally-substituted" refers to the possible presence of one or more pendant substituents in which one or more hydrogen atoms is replaced by groups independently selected from $C_1$-$C_6$ alkyl, $C_1$-$C_6$ alkoxy, oxo (which may be represented in the tautomeric enol form), carboxyl, amino, hydroxy (which when present in an enol system may be represented in the tautomeric keto form), nitro, sulphono, sulphanyl, $C_1$-$C_6$ carboxyl, $C_1$-$C_6$ alkoxycarbonyl, $C_1$-$C_6$ alkylcarbonyl, formyl, aryl, aryloxy, aryloxycarbonyl, arylcarbonyl, heteroaryl, amino, mono- and di($C_1$-$C_6$ alkyl)amino; carbamoyl, mono- and di($C_1$-$C_6$)aminocarbonyl, amino-$C_1$-$C_6$ alkylaminocarbonyl, mono- and di($C_1$-$C_6$ alkyl)amino-$C_1$-$C_6$ alkyl-aminocarbonyl, $C_1$-$C_6$ alkylcarbonylamino, cyano, guanidino, carbamido, $C_1$-$C_6$ alkanoyloxy, $C_1$-$C_6$ alkylsulphonyloxy, dihalogen-$C_1$-$C_6$-alkyl, trihalogen-$C_1$-$C_6$, halogen, where aryl and heteroaryl representing substituents maybe substituted one or more times with $C_1$-$C_6$ alkyl, $C_1$-$C_6$ alkoxy, nitro, cyano, hydroxy, amino or halogen. In general, the above substituents may be susceptible to further optional substitution. Furthermore, the phrase "optionally-substituted X, Y and Z" is to be interpreted to mean that each of X, Y and Z is optionally-substituted unless otherwise indicated.

Many of the compounds here are disclosed as hydrochloride or other salts, but those skilled in medicinal chemistry will appreciate that the choice of salt is not critical, and other pharmaceutically-acceptable salts can be prepared by well-known methods. Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499 discuss such salts in detail.

More generally, those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, 13C for carbon, 15N for nitrogen) can also be readily produced. All such derivatives are contemplated within the scope of this disclosure.

Certain compounds of the disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)-or, as (D)-or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)- isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the compounds are within the scope of the disclosure.

The present application discloses pharmaceutical compositions containing one or more compounds of formula (I) with a pharmaceutically acceptable carrier. Pharmaceutical compositions containing one or more of the compounds described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions disclosed here, one or more of the disclosed compounds is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Tablets and capsules may include solid pharmaceutical carriers. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, and the like, an amount of the active ingredient necessary to deliver the desired dose. The pharmaceutical compositions herein will contain, per unit dosage unit, e.g., tablet, capsule, powder, injection, suppository, and the like, of from about 50-100 mg and may be given at a dosage of from about 0.1-5.0 mg/kg/day, preferably from about 0.5-2.5 mg/kg/day. Determination of the appropriate dosage of drugs generally is well within the ability of those skilled in pharmacology and clinical medicine, and in the present context may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

In one aspect, the disclosure provides a compound of Formula I, wherein the compound is selected from Table 1.

TABLE 1

| # | Structure | Name |
|---|---|---|
| 1 | 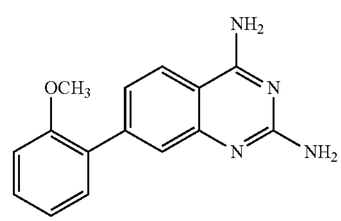 [SMILES: COc1ccccc1-c1ccc2c(N)nc(N)nc2c1] | 7-(2-methoxyphenyl)quinazoline-2,4-diamine |
| 2 | 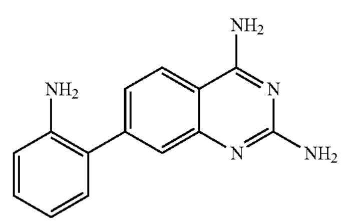 [SMILES: Nc1nc(N)c2ccc(-c3ccccc3N)cc2n1] | 7-(2-aminophenyl)quinazoline-2,4-diamine |
| 3 | 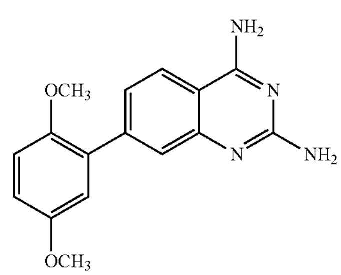 [SMILES: COc1ccc(OC)c(-c2ccc3c(N)nc(N)nc3c2)c1] | 7-(2,5-dimethoxyphenyl) quinazoline-2,4-diamine |

TABLE 1-continued

| # | Structure | Name |
|---|---|---|
| 4 | 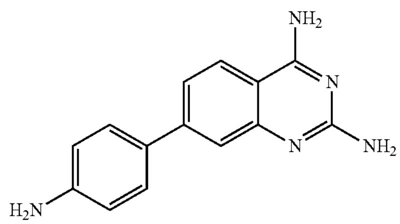 [SMILES: Nc1ccc(-c2ccc3c(N)nc(N)nc3c2)cc1] | 7-(4-aminophenyl)quinazoline-2,4-diamine |
| 5 | 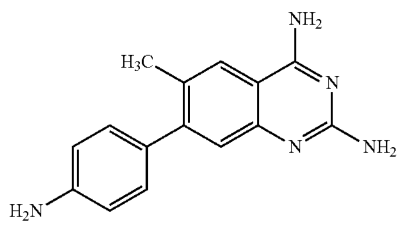 [SMILES: Cc1cc2c(N)nc(N)nc2cc1-c1ccc(N)cc1] | 7-(4-aminophenyl)-6-methylquinazoline-2,4-diamine |
| 6 | 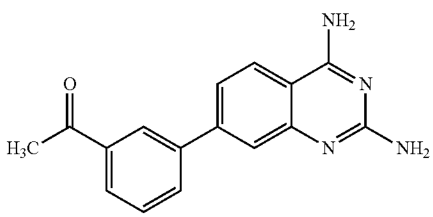 [SMILES: CC(=O)c1cccc(-c2ccc3c(N)nc(N)nc3c2)c1] | 1-(3-(2,4-diaminoquinazolin-7-yl)-phenyl)ethanone |
| 7 | 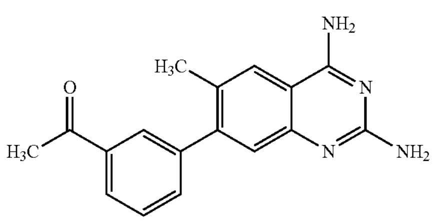 [SMILES: CC(=O)c1cccc(-c2cc3nc(N)nc(N)c3cc2C)c1] | 1-(3-(2,4-diamino-6-methyl quinazolin-7-yl)-phenyl)ethanone |
| 8 | 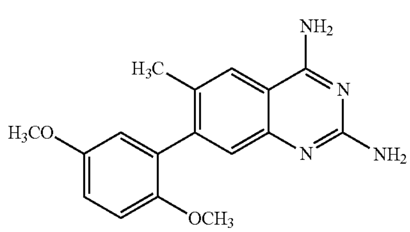 [SMILES: COc1ccc(OC)c(-c2cc3nc(N)nc(N)c3cc2C)c1] | 7-(2,5-dimethoxyphenyl)-6-methylquin-azoline-2,4-diamine |
| 9 | 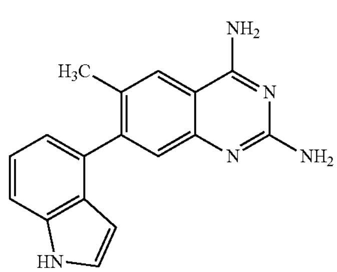 [SMILES: Cc1cc2c(N)nc(N)nc2cc1-c1cccc2[nH]ccc12] | 7-(1H-indol-4-yl)-6-methylquinazoline-2,4-diamine |

TABLE 1-continued

| # | Structure | Name |
|---|---|---|
| 10 | 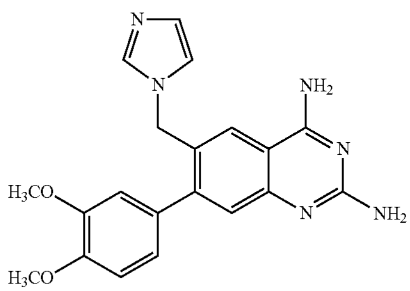 [SMILES: COc1ccc(-c2cc3nc(N)nc(N)c3cc2Cn2ccnc2)cc1OC] | 6-((1H-imidazol-1-yl)methyl)-7-(3,4-dimethoxyphenyl)quinazoline-2,4-diamine |
| 11 | 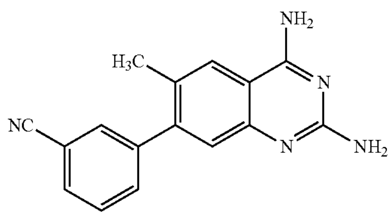 [SMILES: Cc1cc2c(N)nc(N)nc2cc1-c1cccc(C#N)c1] | 3-(2,4-diamino-6-methylquinazolin-7-yl)benzonitrile |
| 12 | 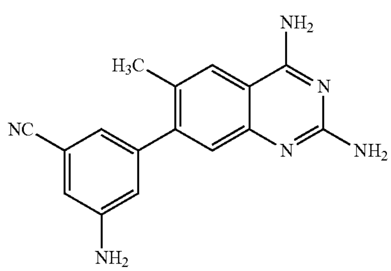 [SMILES: Cc1cc2c(N)nc(N)nc2cc1-c1cc(N)cc(C#N)c1] | 3-amino-5-(2,4-diamino-6-methylquin-azolin-7-yl)benzonitrile |
| 13 | 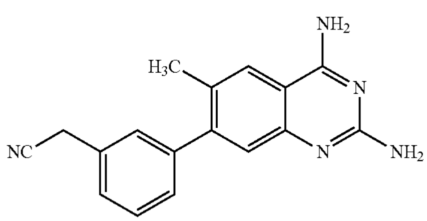 [SMILES: Cc1cc2c(N)nc(N)nc2cc1-c1cccc(CC#N)c1] | 2-(3-(2,4-diamino-6-methylquinazolin-7-yl)-phenyl)acetonitrile |
| 14 | 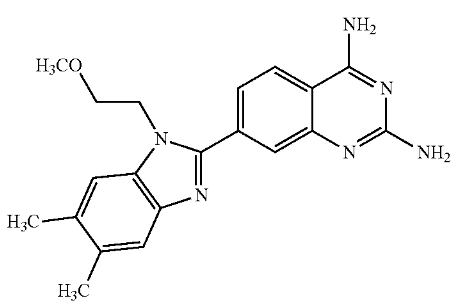 [SMILES: COCCn1c(-c2ccc3c(N)nc(N)nc3c2)nc2cc(C)c(C)cc21] | 7-(1-(2-methoxyethyl)-5,6-dimethyl-1H-benzo[d]-imidazol-2-yl)quinazoline-2,4-diamine |

TABLE 1-continued

| # | Structure | Name |
|---|-----------|------|
| 15 | 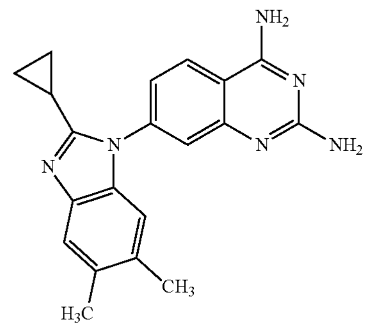 [SMILES: Cc1cc2nc(C3CC3)n(-c3ccc4c(N)nc(N)nc4c3)c2cc1C] | 7-(2-cyclopropyl-5,6-dimethyl-1H-benzo[d]-imidazol-1-yl)quinazoline-2,4-diamine |
| 16 | 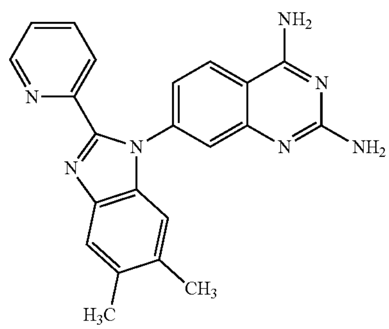 [SMILES: Cc1cc2nc(-c3ccccn3)n(-c3ccc4c(N)nc(N)nc4c3)c2cc1C] | 7-(5,6-dimethyl-2-(pyridin-2-yl)-1H-benzo[d]-imidazol-1-yl)quinazoline-2,4-diamine |
| 17 | 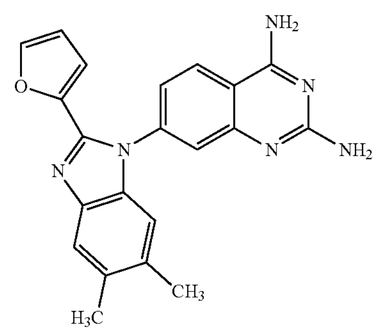 [SMILES: Cc1cc2nc(-c3ccco3)n(-c3ccc4c(N)nc(N)nc4c3)c2cc1C] | 7-(2-(furan-2-yl)-5,6-dimethoxy-1H-benzo[d]-imidazol-1-yl)quinazoline-2,4-diamine |
| 18 | 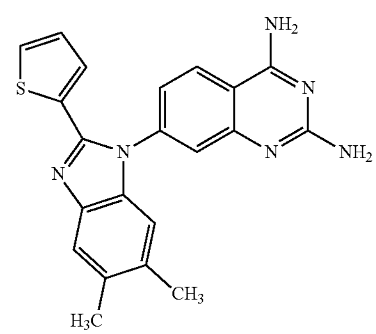 [SMILES: Cc1cc2nc(-c3cccs3)n(-c3ccc4c(N)nc(N)nc4c3)c2cc1C] | 7-(5,6-dimethyl-2-(thiophen-2-yl)-1H-benzo[d]-imidazol-1-yl)quinazoline-2,4-diamine |

TABLE 1-continued

| # | Structure | Name |
|---|---|---|
| 19 | 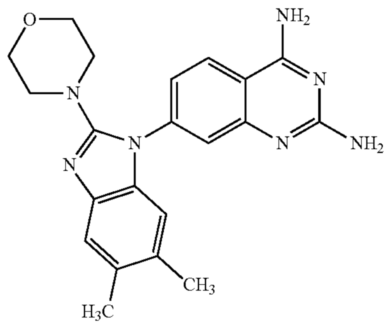 [SMILES: Cc1cc2nc(N3CCOCC3)n(-c3ccc4c(N)nc(N)nc4c3)c2cc1C] | 7-(5,6-dimethyl-2-morpholino-1H-benzo[d]-imidazol-1-yl)quinazoline-2,4-diamine |
| 20 | 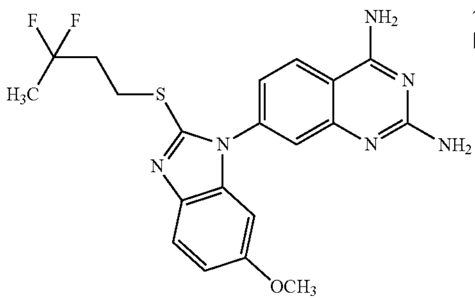 | 7-(2-(3,3-difluorobutylthio)-6-methoxy-1H-benzo-[d]imidazol-1-yl)quinazoline-2,4-diamine |
| 21 | 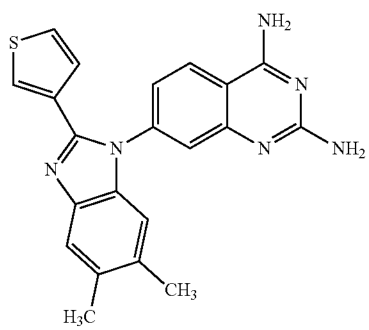 [SMILES: Cc1cc2nc(-c3ccsc3)n(-c3ccc4c(N)nc(N)nc4c3)c2cc1C] | 7-(5,6-dimethyl-2-(thiophen-3-yl)-1H-benzo[d]-imidazol-1-yl)quinazoline-2,4-diamine |
| 22 | 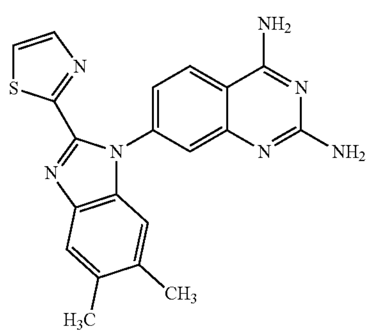 [SMILES: Cc1cc2nc(-c3nccs3)n(-c3ccc4c(N)nc(N)nc4c3)c2cc1C] | 7-[5,6-dimethyl-2-(thiazol-2-yl)-1H-benzo[d]-imidazol-1-yl]quinazoline-2,4-diamine |
| 23 | 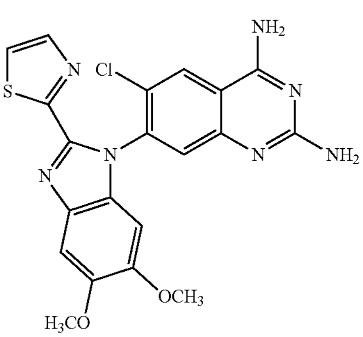 [SMILES: COc1cc2nc(-c3nccs3)n(-c3cc4nc(N)nc(N)c4cc3Cl)c2cc1OC] | 6-chloro-7-(5,6-dimethoxy-2-(thiazol-2-yl)-1H-benzo[d]imidazol-1-yl)quinazo-line-2,4-diamine |

TABLE 1-continued
| # | Structure | Name |
|---|---|---|
| 24 | 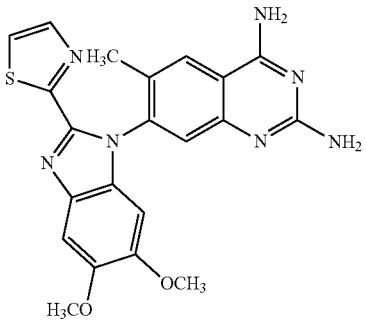 [SMILES: COc1cc2nc(-c3nccs3)n(-c3cc4nc(N)nc(N)c4cc3C)c2cc1OC] | 7-(5,6-dimethoxy-2-(thiazol-2-yl)-1H-benzo[d]-imidazol-1-yl)-6-methylquin-azoline-2,4-diamine |
| 25 | 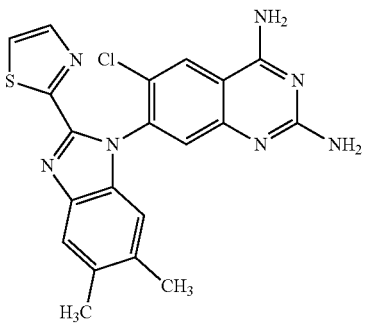 [SMILES: Cc1cc2nc(-c3nccs3)n(-c3cc4nc(N)nc(N)c4cc3Cl)c2cc1C] | 6-chloro-7-(5,6-dimethyl-2-(thiazol-2-yl)-1H-benzo[d]imidazol-1-yl)quinazoline-2,4-diamine |
| 26 | 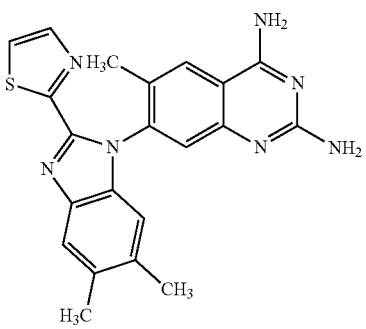 [SMILES: Cc1cc2nc(-c3nccs3)n(-c3cc4nc(N)nc(N)c4cc3C)c2cc1C] | 7-(5,6-dimethyl-2-(thiazol-2-yl)-1H-benzo[d]-imidazol-1-yl)-6-methylquin-azoline-2,4-diamine |
| 27 | 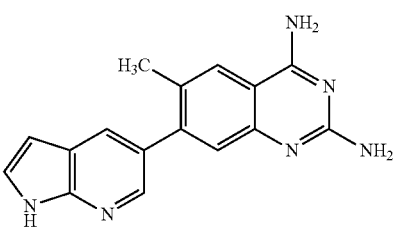 [SMILES: Cc1cc2c(N)nc(N)nc2cc1-c1cnc2[nH]ccc2c1] | 6-methyl-7-(1H-pyrrolo[2,3-b]pyridin-5-yl)quin-azoline-2,4-diamine |
| 28 | 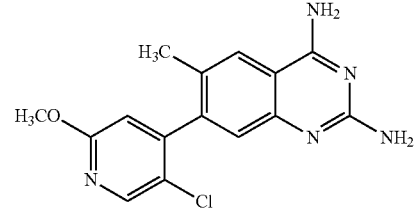 [SMILES: COc1cc(-c2cc3nc(N)nc(N)c3cc2C)c(Cl)cn1] | 7-(5-chloro-2-methoxypyridin-4-yl)-6-methylquin-azoline-2,4-diamine |

TABLE 1-continued

| # | Structure | Name |
|---|---|---|
| 29 | 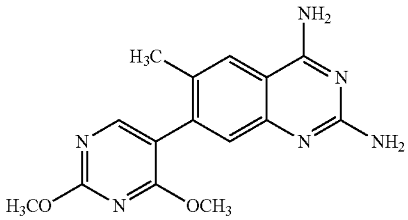 [SMILES: COc1ncc(-c2cc3nc(N)nc(N)c3cc2C)c(OC)n1] | 7-(2,4-dimethoxypyrimidin-5-yl)-6-methylquinazoline-2,4-diamine |
| 30 | 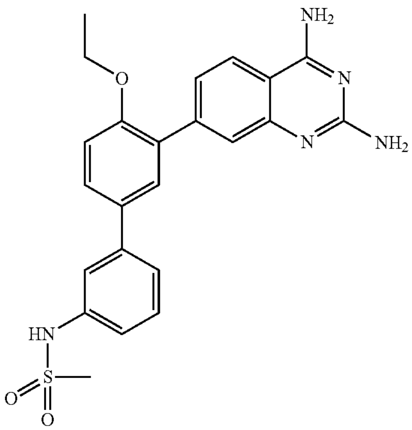 [SMILES: CCOc1ccc(-c2cccc(NS(C)(=O)=O)c2)cc1-c1ccc2c(N)nc(N)nc2c1] | N-(3'-(2,4-diaminoquinoazlin-7-yl)-4'-ethoxybiphenyl-3-yl)methanesulfonamide |
| 31 | 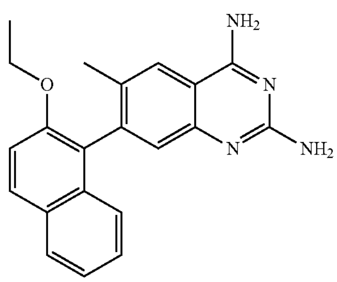 [SMILES: CCOc1ccc2ccccc2c1-c1cc2nc(N)nc(N)c2cc1C] | 7-(2-ethoxynaphthalen-1-yl)-6-methylquinazoline-2,4-diamine |
| 32 | 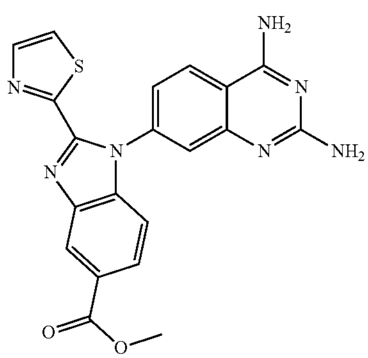 [SMILES: COC(=O)c1ccc2c(c1)nc(-c1nccs1)n2-c1ccc2c(N)nc(N)nc2c1] | methyl 1-(2,4-diaminoquinazolin-7-yl)-2-(thiazol-2-yl)-1H-benzo[d]imidazole-5-carboxylate |
| 33 | 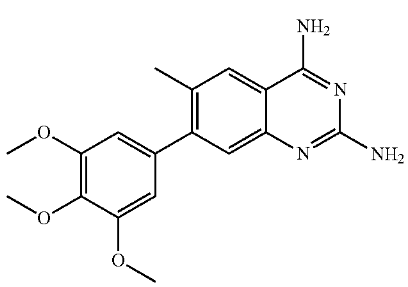 [SMILES: COc1cc(-c2cc3nc(N)nc(N)c3cc2C)cc(OC)c1OC] | 6-methyl-7-(3,4,5-trimethoxyphenyl) quinazoline-2,4-diamine |

TABLE 1-continued

| # | Structure | Name |
|---|---|---|
| 34 | 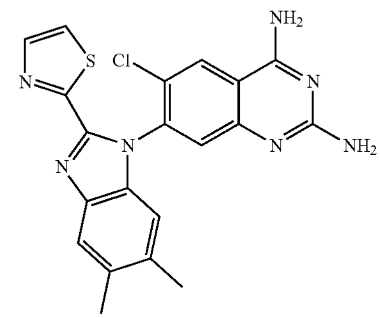 [SMILES: Cc1cc2nc(-c3nccs3)n(-c3cc4nc(N)nc(N)c4cc3Cl)c2cc1C] | 6-chloro-7-(5,6-dimethyl-2-(thiazol-2-yl)-1H-benzo[d]imidazol-1-yl)quinazoline-2,4-diamine |
| 35 | 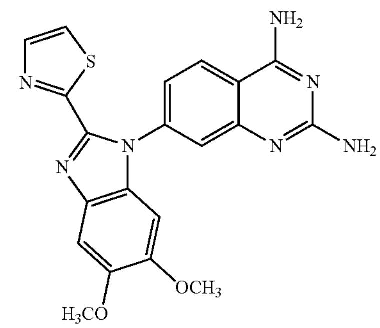 [SMILES: COc1cc2nc(-c3nccs3)n(-c3ccc4c(N)nc(N)nc4c3)c2cc1OC] | 7-(5,6-dimethoxy-2-thiazol-2-yl)-1H-benzo[d]imidazol-1-yl)quinazoline-2,4-diamine |
| 36 | 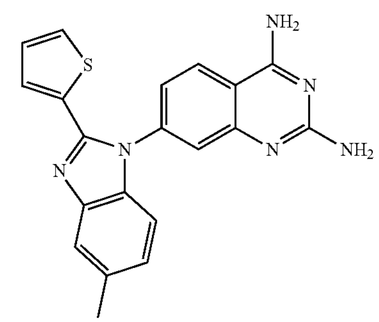 [SMILES: Cc1ccc2c(c1)nc(-c1cccs1)n2-c1ccc2c(N)nc(N)nc2c1] | 7-(5-methyl-2-thiophen-2-yl)-1H-benzo[d]imidazol-1-yl)quinazoline-2,4-diamine |
| 37 | 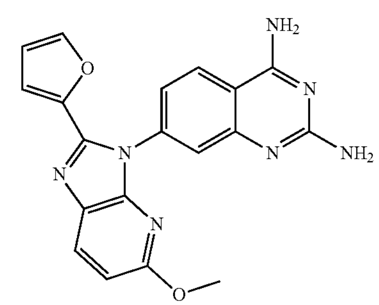 [SMILES: COc1ccc2nc(-c3ccco3)n(-c3ccc4c(N)nc(N)nc4c3)c2n1] | 7-(2-furan-2-yl)-5-methoxy-3H-imidazo[4,5-b]pyridine-3-yl)quinazoline-2,4-diamine |
| 38 | 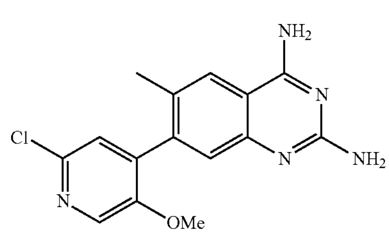 [SMILES: COc1cnc(Cl)cc1-c1cc2nc(N)nc(N)c2cc1C] | 7-(2-chloro-5-methyloxypyridin-4-yl)-6-methylquinazoline-2,4-diamine |

TABLE 1-continued

| # | Structure | Name |
|---|---|---|
| 39 | 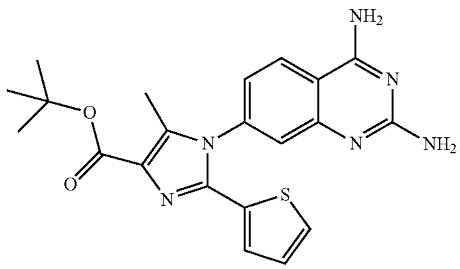 [SMILES: Cc1c(C(=O)OC(C)(C)C)nc(-c2cccs2)n1-c1ccc2c(N)nc(N)nc2c1] | tert-butyl 1-(2,4-diaminoquinazolin-7-yl)-5-methyl-2-thiophen-2-yl)-1H-imidazole-4-carboxylate |
| 40 | 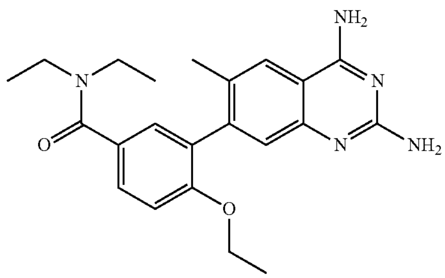 [SMILES: CCOc1ccc(C(=O)N(CC)CC)cc1-c1cc2nc(N)nc(N)c2cc1C] | 3-(2,4-diamino-6-methylquinazolin-7-yl)-4-ethoxy-N,N-diethylbenzamide |
| 41 | 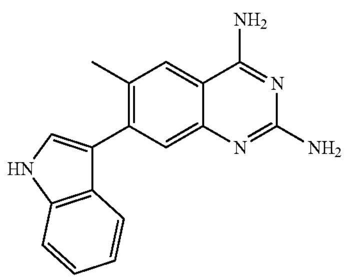 [SMILES: Cc1cc2c(N)nc(N)nc2cc1-c1c[nH]c2ccccc12] | 7-(1H-indol-3-yl)-6-methylquinazoline-2,4-diamine |

In another aspect, the disclosure provides a pharmaceutical composition of a compound of Formula I together with a pharmaceutically acceptable carrier.

In another aspect, the disclosure provides methods for impeding growth of a bacterium by exposing the bacteria to a compound of Formula I.

In another aspect, the disclosure provides methods for treating a mammal prophylactically or therapeutically for a bacterial infection by administering to the mammal a compound of Formula I.

In another aspect, the disclosure provides methods for treating a mammal prophylactically or therapeutically for a bacterial infection comprising administering to the mammal a pharmaceutical composition composition of a compound of Formula I together with a pharmaceutically acceptable carrier.

In another aspect, the disclosure provides methods for inhibiting DHFR activity by contacting the DHFR enzyme with an amount of a compound of Formula I effective for such inhibition.

In another aspect, the disclosure provides methods for treating cell proliferative diseases, autoimmune disease, inflammatory disease or bacterial, fungal or parasitic infection, by administering to a subject in need thereof, an effective amount of a compound of Formula I.

In another aspect, the disclosure provides methods for treating cell proliferative diseases, autoimmune disease, inflammatory disease or bacterial, fungal or parasitic infection, by administering to a subject in need thereof, an effective amount of a compound of Formula I, wherein the disease is cancer, rheumatoid arthritis, or fungal, bacterial or parasitic infection.

EXAMPLES

Some aspects of the disclosure can be further illustrated by the following non-limiting examples.

General Procedure for the Preparation of Diaminoquinazolines:

General procedures for the preparation of the diaminoquinazoline

Scheme 1

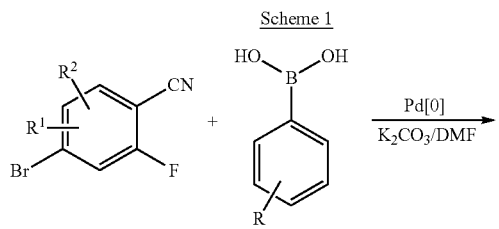

-continued
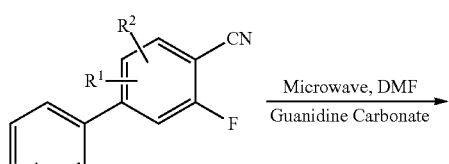
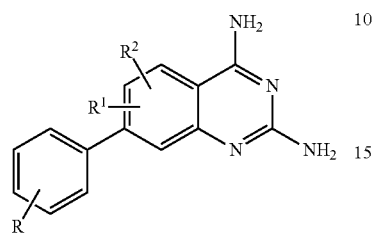
Scheme 2
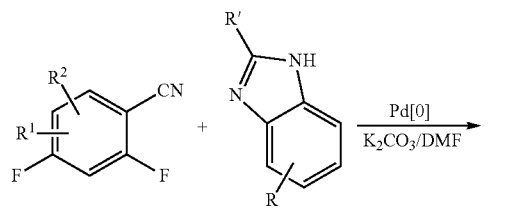
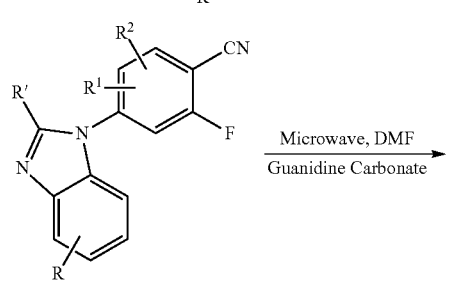
Scheme 3
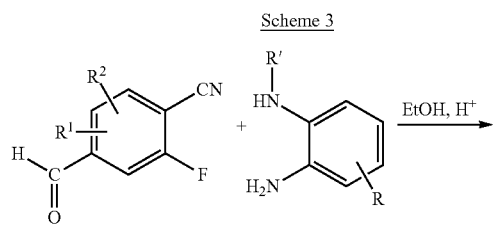
-continued
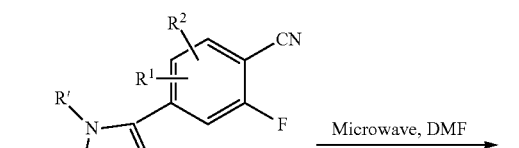
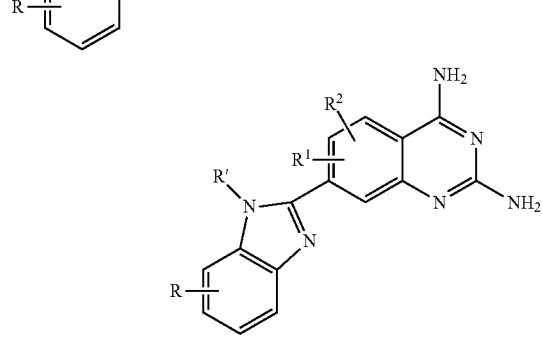
Scheme 4
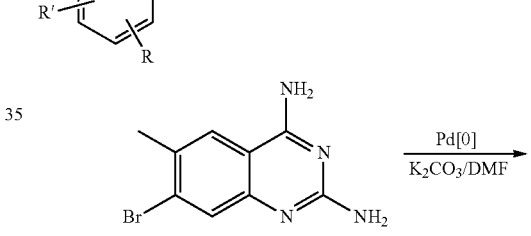
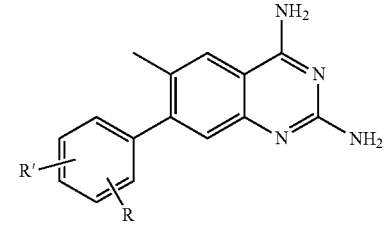
Specific examples of diaminoquinazoline compounds prepared by these methods are provided in Schemes 5-7.
Scheme 5
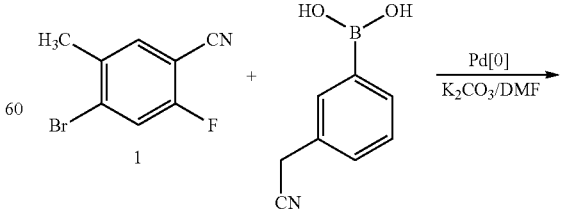

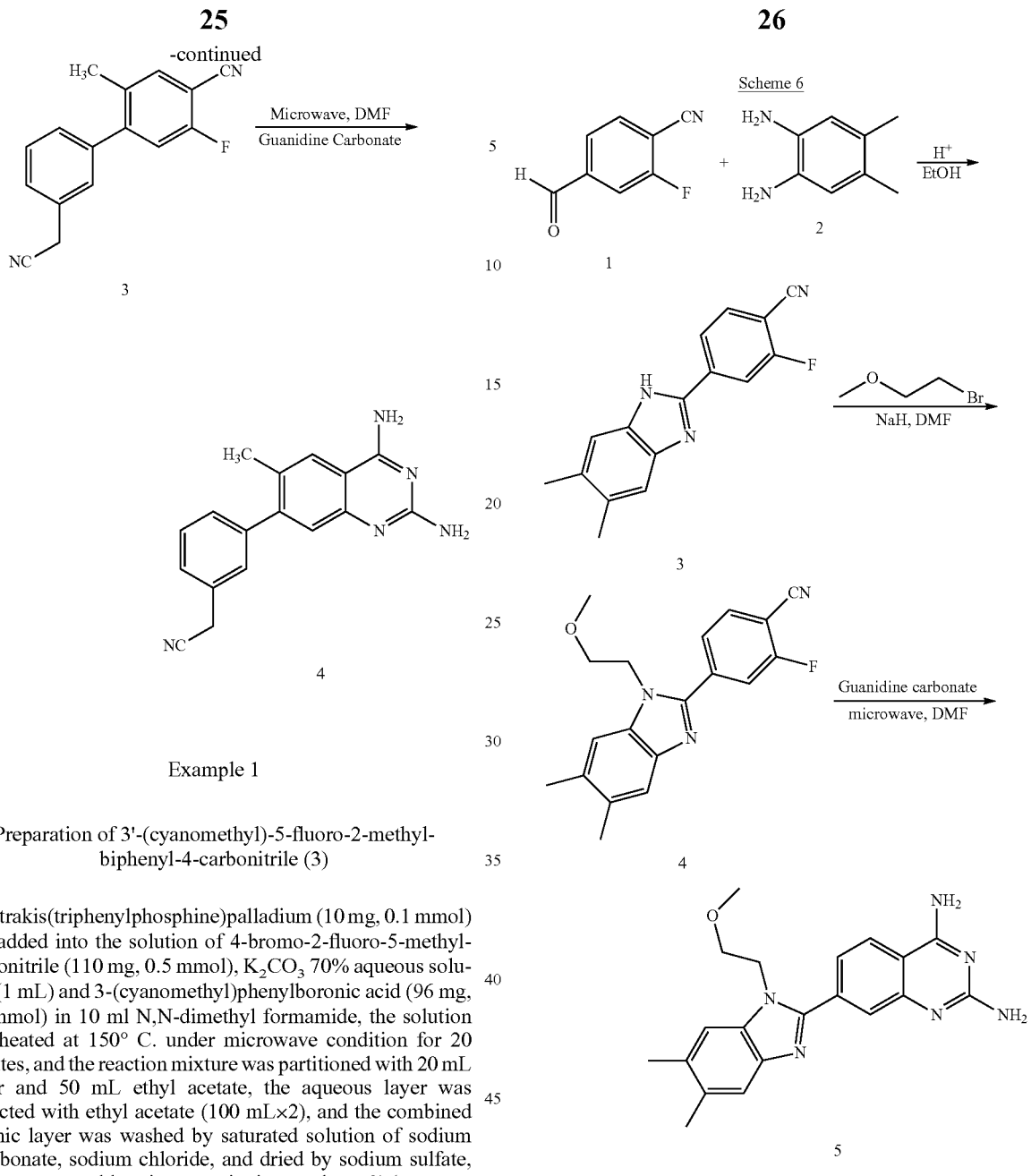

Example 1

Preparation of 3'-(cyanomethyl)-5-fluoro-2-methyl-biphenyl-4-carbonitrile (3)

Tetrakis(triphenylphosphine)palladium (10 mg, 0.1 mmol) was added into the solution of 4-bromo-2-fluoro-5-methylbenzonitrile (110 mg, 0.5 mmol), $K_2CO_3$ 70% aqueous solution (1 mL) and 3-(cyanomethyl)phenylboronic acid (96 mg, 0.6 mmol) in 10 ml N,N-dimethyl formamide, the solution was heated at 150° C. under microwave condition for 20 minutes, and the reaction mixture was partitioned with 20 mL water and 50 mL ethyl acetate, the aqueous layer was extracted with ethyl acetate (100 mL×2), and the combined organic layer was washed by saturated solution of sodium bicarbonate, sodium chloride, and dried by sodium sulfate, and concentrated by give quantitative products 3'-(cyanomethyl)-5-fluoro-2-methylbiphenyl-4-carbonitrile 3 (114 mg, 88% yield, confirmed by LCMS: 251.10) without purification for next steps.

Example 2

Preparation of 2-(3-(2,4-diamino-6-methylquinazolin-7-yl)phenyl)-aceto-nitrile (4)

To the above solution of 3'-(cyanomethyl)-5-fluoro-2-methylbiphenyl-4-carbonitrile 3 was added guanidine carbonate (180 mg, 0.5 mmol) and N,N-dimethyl formamide (5 mL). The reaction was heated at 150° C. under microwave condition for 20 minutes. The mixture was purified by high performance liquid chromatography to yield compound 4 as white solid trifluoroacetic acid salt (89 mg, Yield: 68%, confirmed by LCMS: 290.15 and HPLC).

Example (3)

Preparation of 4-(5,6-dimethyl-1H-benzo[d]imidazol-2-yl)-2-fluorobenzo-nitrile (3)

To a solution of 2-fluoro-4-formylbenzonitrile 1 (100 mg, 0.7 mmol) and 4,5-dimethyl benzene-1,2-diamine 2 (109 mg, 0.8 mmol) in ethanol (10 ml) was added a catalytic amount of p-toluenesulfonic acid (0.5 mg, 0.5 mmol). The mixture was stirred reflux for 2 hours and concentrated by rotor evaporation. The crude material was purified through column chromatography with 40% ethyl acetate in hexane to yield compound 3 as white solid (68% yield, 121 mg, confirmed by LCMS: 266.20).

Example (4)

Preparation of 2-fluoro-4-(1-(2-methoxyethyl)-5,6-dimethyl-1H-benzo[d]imidazol-2-yl)benzonitrile (4)

4-(5,6-dimethyl-1H-benzo[d]imidazol-2-yl)-2-fluorobenzonitrile 3 (110 mg, 0.4 mmol) was combined with 1-bromo-2-methoxyethane (76 mg, 0.55 mmol), NaH (13 mg, 0.55 mmol), and N,N-dimethyl formamide (5 ml). The reaction was heated at 100° C. for 1.5 hours. The product solution (confirmed by LCMS: 324.22) was carried on to the next step without purification.

Example 5

Preparation of 2-fluoro-4-(1-(2-methoxyethyl)-5,6-dimethyl-1H-benzo[d]imidazol-2-yl)benzonitrile (5)

To the above solution of 2-fluoro-4-(1-(2-methoxyethyl)-5,6-dimethyl-1H-benzo[d]imidazol-2-yl)benzonitrile 4 was added guanidine carbonate (180 mg, 0.5 mmol) and N,N-dimethyl formamide (5 mL). The reaction was heated at 150° C. under microwave condition for 20 minutes. The mixture was purified by high performance liquid chromatography to yield compound 5 as white solid trifluoroacetic acid salt (96 mg, Yield: 64%, confirmed by LCMS: 363.15 and HPLC).

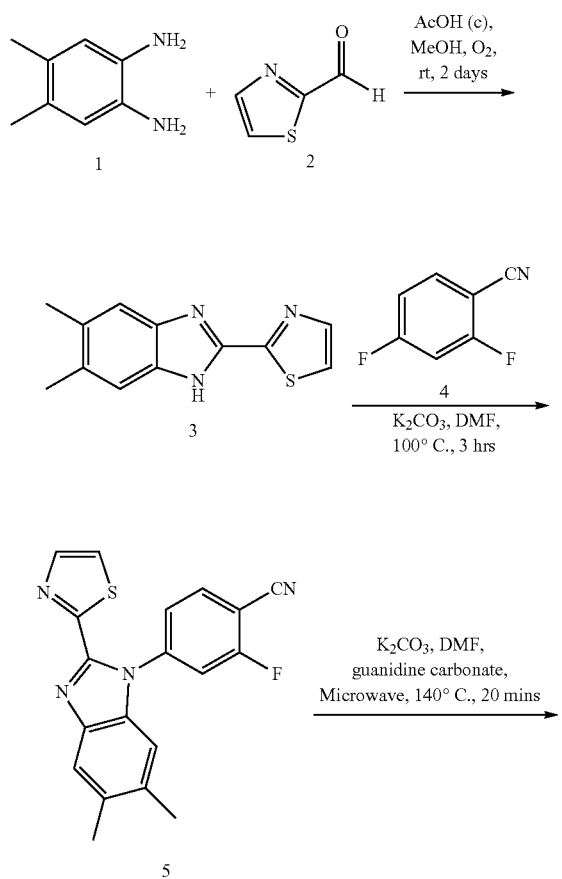

Scheme 7

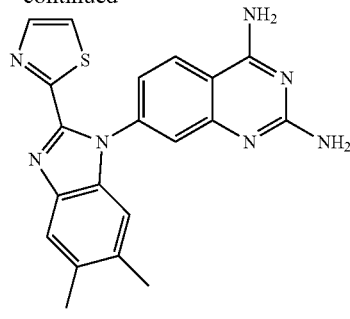

6

Example 6

General Method for the Preparation of 7-(benzimidaol-1-yl)-2,4-diaminoquinazolines The Preparation of 2-(5,6-dimethyl-1H-benzo[d]imidazol-2-yl)thiazole (3): To a well-dissolved solution of 4,5-dimethyl-1,2-phenylenediamine (1.382 g, 10 mmol) in methanol (75 ml) was added catalytic amount of acetic acid (121 mg, 2 mmol) followed by the drop-wise addition over 30 minutes of the solution of 2-thiazole carboxaldehyde (1.25 g, 11 mmol) in methanol (25 ml). The resulting mixture was stirred at room temperature while oxygen was gently bubbling through from one-layer balloon for two days. The solvent was then removed by rotor evaporation. The residue was purified through reverse phase chromatography (150 g Teledyne HP C18 column; 35% of $CH_3CN$ (0.1% TFA) in water (0.1% TFA). Acetonitrile in the combined eluates was removed by rotor evaporation, and the resulting aqueous solution was neutralized by sodium bicarbonate. It was then extracted with dichloromethane (150 ml×3). The combined organic layers were dried over magnesium sulfate, and the solvent was taken off by rotor evaporation to afford the title compound as yellow solid (69.4% yield, 2.08 g, confirmed by LCMS: 230.09).

Example 7

Preparation of 4-(5,6-dimethyl-2-(thiazol-2-yl)-1H-benzo[d]imidazol-1-yl)-2-fluorobenzonitrile (5)

2-(5,6-Dimethyl-1H-benzo[d]imidazol-2-yl)thiazole 3 (174 mg, 0.5 mmol) was combined with 2,4-difluorobenzonitrile (76.5 mg, 0.55 mmol), potassium carbonate (139 mg, 1 mmol), and anhydrous N,N-dimethyl formamide (5 mL). The reaction was heated at 100° C. under microwave condition for 3 hours. The crude product solution (confirmed by LCMS: 349.13) was carried on to the next step without purification.

Example 8

Preparation of 7-(5,6-dimethyl-2-(thiazol-2-yl)-1H-benzo[d]imidazol-1-yl)quinazoline-2,4-diamine (6)

To the above solution of 4-(5,6-dimethyl-2-(thiazol-2-yl)-1H-benzo[d]imidazol-1-yl)-2-fluorobenzonitrile 5 was added guanidine carbonate (360.4 mg, 2 mmol), potassium carbonate (552.8 mg, 4 mmol), and anhydrous N,N-dimethyl formamide (2 mL). The reaction was heated at 140° C. under microwave condition for 20 minutes. The mixture was purified by high performance liquid chromatography to yield compound 6 as white solid trifluoroacetic acid salt (80 mg, Yield: 60%, confirmed by LCMS: 388.43 and HPLC).

Example 9

General Method for the Preparation of 7-aryl-2,4-diaminoquiazolines: (Scheme 4)

Tetrakis(triphenylphosphine)palladium (10 mg, 0.1 mmol) was added into the solution of 7-bromo-6-methylquinazoline-2,4-diamine (126 mg, 0.5 mmol), $K_2CO_3$ 70% aqueous solution (1 mL) and substituted arylboronic acid (0.6 mmol) in 10 ml N,N-dimethyl formamide, the solution was heated at 150° C. under microwave condition for 20 minutes, and the reaction mixture was partitioned with 20 mL water and 50 mL ethyl acetate, the aqueous layer was extracted with ethyl acetate (100 mL×2), and the combined organic layer was washed by saturated solution of sodium bicarbonate, sodium chloride, and dried by sodium sulfate, concentrated and the residue was subjected to pre-HPLC separation to give the desired compounds.

Example 10

Preparation of tert-butyl 1-(2,4-diaminoquinazolin-7-yl)-5-methyl-2-thiophen-2-yl)-1H-imidazole-4-carboxylate (compound 39)

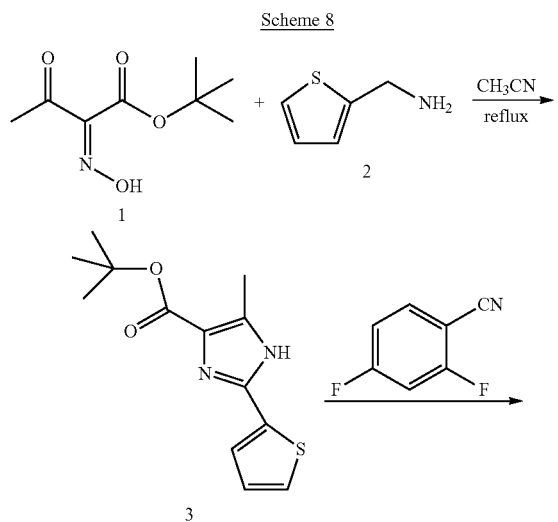

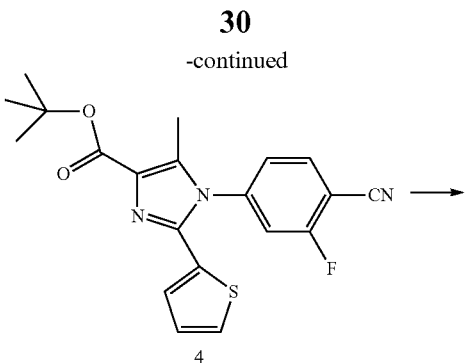

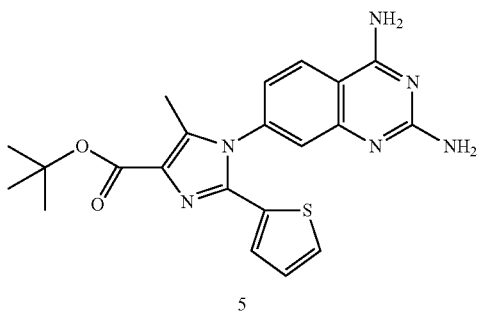

tert-butyl 2-(hydroxyimino)-3-oxobutanoate 1 (1.85 g, 9.89 mmol) was mixed with thiophen-2-ylmethanamine 2 (1.07 mL, 10.44 mmol) in anhydrous acetonitrile (30 mL). The resulting mixture was heated to reflux for 3 hrs, upon cooling, the suspension was filtered, and the filtered material was washed with a small amount of acetonitrile to afford the desired solid product 3 (LC-MS: 265.10). Compound 3 was converted to tert-butyl 1-(2,4-diaminoquinazolin-7-yl)-5-methyl-2-thiophen-2-yl)-1H-imidazole-4-carboxylate 5 (compound 39) by the method described in Examples 6-9.

Further examples of diaminoquinazoline compounds prepared by these methods are provided in

TABLE 2

| # | Structure | Name |
|---|---|---|
| 1 | 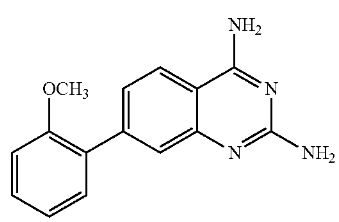 [SMILES: COc1ccccc1-c1ccc2c(N)nc(N)nc2c1] | 7-(2-methoxyphenyl)quinazoline-2,4-diamine |

TABLE 2-continued

| # | Structure | Name |
|---|---|---|
| 2 | 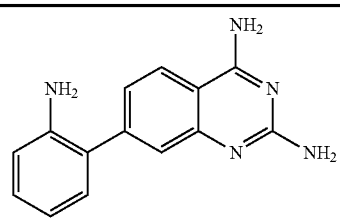 | 7-(2-aminophenyl)quinazoline-2,4-diamine |
| 3 | 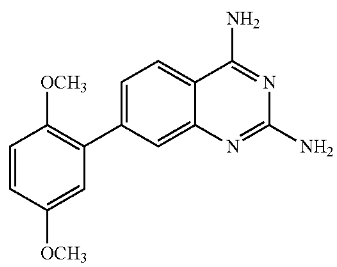 [SMILES: COc1ccc(OC)c(-c2ccc3c(N)nc(N)nc3c2)c1] | 7-(2,5-dimethoxyphenyl) quinazoline-2,4-diamine |
| 4 | 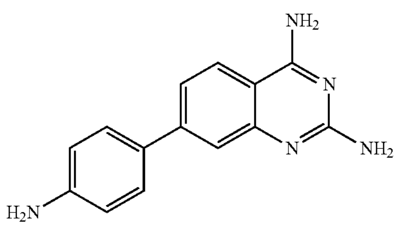 [SMILES: Nc1ccc(-c2ccc3c(N)nc(N)nc3c2)cc1] | 7-(4-aminophenyl)quinazoline-2,4-diamine |
| 5 | 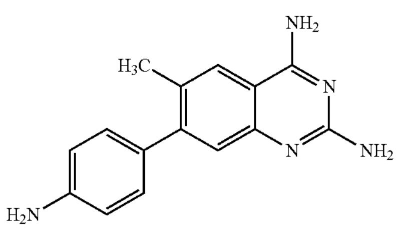 [SMILES: Cc1cc2c(N)nc(N)nc2cc1-c1ccc(N)cc1] | 7-(4-aminophenyl)-6-methylquinazoline-2,4-diamine |
| 6 | 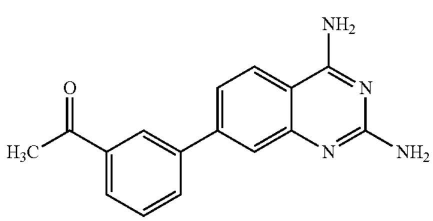 [SMILES: CC(=O)c1cccc(-c2ccc3c(N)nc(N)nc3c2)c1] | 1-(3-(2,4-diaminoquinazolin-7-yl)-phenyl)ethanone |
| 7 | 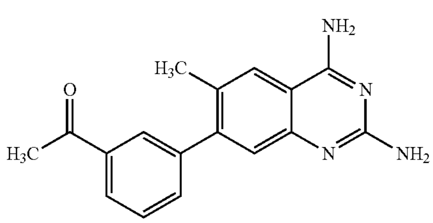 [SMILES: CC(=O)c1cccc(-c2cc3nc(N)nc(N)c3cc2C)c1] | 1-(3-(2,4-diamino-6-methyl quinazolin-7-yl)-phenyl)ethanone |
| 8 | 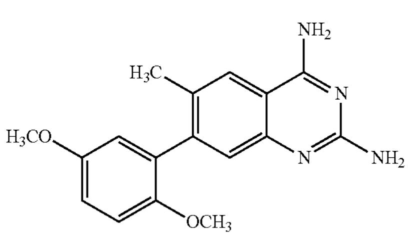 [SMILES: COc1ccc(OC)c(-c2cc3nc(N)nc(N)c3cc2C)c1] | 7-(2,5-dimethoxyphenyl)-6-methylquin-azoline-2,4-diamine |

TABLE 2-continued
| # | Structure | Name |
|---|---|---|
| 9 | 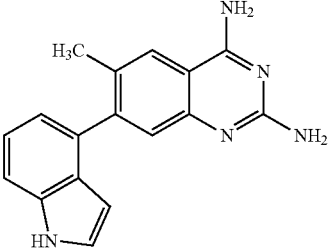 [SMILES: Cc1cc2c(N)nc(N)nc2cc1-c1cccc2[nH]ccc12] | 7-(1H-indol-4-yl)-6-methylquinazoline-2,4-diamine |
| 10 | 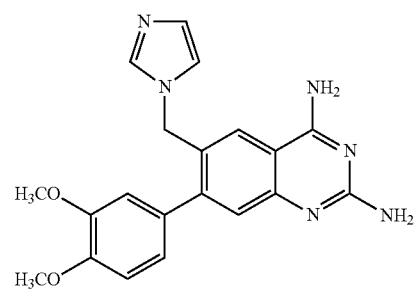 [SMILES: COc1ccc(-c2cc3nc(N)nc(N)c3cc2Cn2ccnc2)cc1OC] | 6-((1H-imidazol-1-yl)methyl)-7-(3,4-dimethoxyphenyl)quinazoline-2,4-diamine |
| 11 | 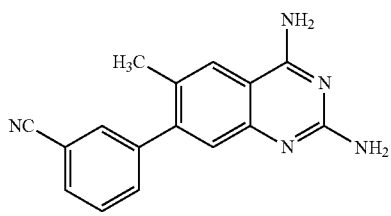 [SMILES: Cc1cc2c(N)nc(N)nc2cc1-c1cccc(C#N)c1] | 3-(2,4-diamino-6-methylquinazolin-7-yl)benzonitrile |
| 12 | 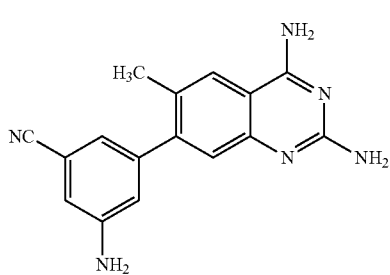 [SMILES: Cc1cc2c(N)nc(N)nc2cc1-c1cc(N)cc(C#N)c1] | 3-amino-5-(2,4-diamino-6-methylquin-azolin-7-yl)benzonitrile |
| 13 | 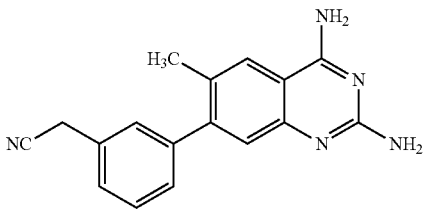 [SMILES: Cc1cc2c(N)nc(N)nc2cc1-c1cccc(CC#N)c1] | 2-(3-(2,4-diamino-6-methylquinazolin-7-yl)-phenyl)acetonitrile |
| 14 | 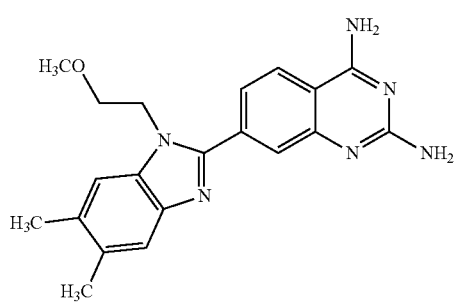 | 7-(1-(2-methoxyethyl)-5,6-dimethyl-1H-benzo[d]-imidazol-2-yl)quinazoline-2,4-diamine |

TABLE 2-continued

| # | Structure | Name |
|---|---|---|
| 15 | 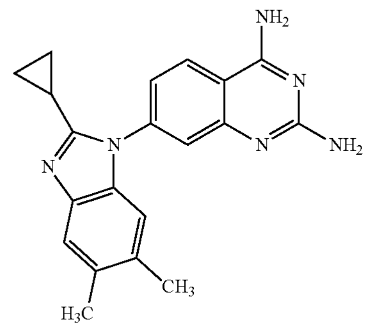 [SMILES: Cc1cc2nc(C3CC3)n(-c3ccc4c(N)nc(N)nc4c3)c2cc1C] | 7-(2-cyclopropyl-5,6-dimethyl-1H-benzo[d]-imidazol-1-yl)quinazoline-2,4-diamine |
| 16 | 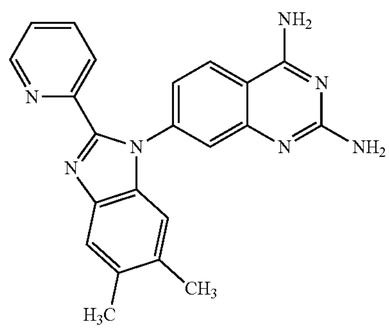 [SMILES: Cc1cc2nc(-c3ccccn3)n(-c3ccc4c(N)nc(N)nc4c3)c2cc1C] | 7-(5,6-dimethyl-2-(pyridin-2-yl)-1H-benzo[d]-imidazol-1-yl)quinazoline-2,4-diamine |
| 17 | 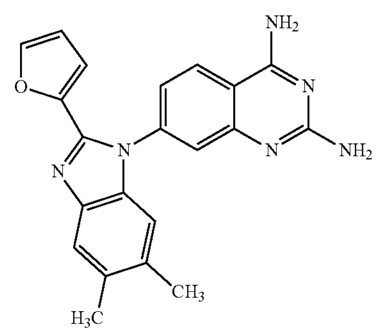 [SMILES: Cc1cc2nc(-c3ccco3)n(-c3ccc4c(N)nc(N)nc4c3)c2cc1C] | 7-(2-(furan-2-yl)-5,6-dimethoxy-1H-benzo[d]-imidazol-1-yl)quinazoline-2,4-diamine |
| 18 | 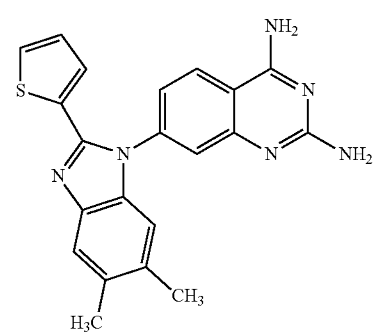 [SMILES: Cc1cc2nc(-c3cccs3)n(-c3ccc4c(N)nc(N)nc4c3)c2cc1C] | 7-(5,6-dimethyl-2-(thiophen-2-yl)-1H-benzo[d]-imidazol-1-yl)quinazoline-2,4-diamine |

TABLE 2-continued

| # | Structure | Name |
|---|---|---|
| 19 | 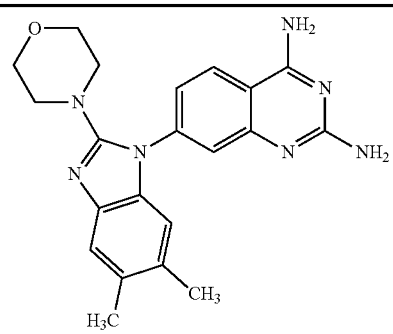 | 7-(5,6-dimethyl-2-morpholino-1H-benzo[d]-imidazol-1-yl)quinazoline-2,4-diamine |
| 20 | 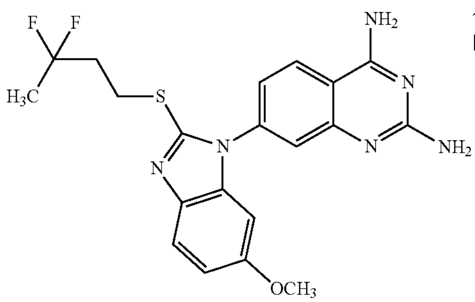 | 7-(2-(3,3-difluorobutylthio)-6-methoxy-1H-benzo-[d]imidazol-1-yl)quinazoline-2,4-diamine |
| 21 | 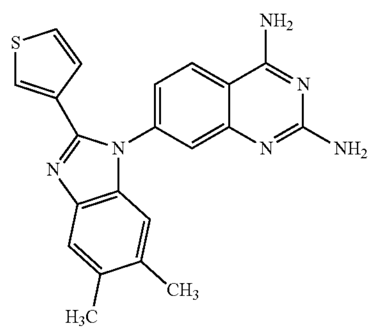 [SMILES: Cc1cc2nc(-c3ccsc3)n(-c3ccc4c(N)nc(N)nc4c3)c2cc1C] | 7-(5,6-dimethyl-2-(thiophen-3-yl)-1H-benzo[d]-imidazol-1-yl)quinazoline-2,4-diamine |
| 22 | 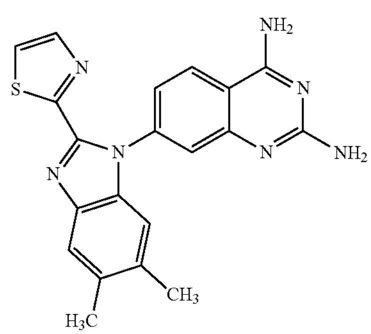 [SMILES: Cc1cc2nc(-c3nccs3)n(-c3ccc4c(N)nc(N)nc4c3)c2cc1C] | 7-[5,6-dimethyl-2-(thiazol-2-yl)-1H-benzo[d]-imidazol-1-yl]quinazoline-2,4-diamine |
| 23 | 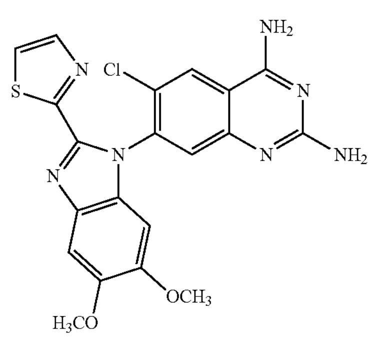 [SMILES: COc1cc2nc(-c3nccs3)n(-c3cc4nc(N)nc(N)c4cc3Cl)c2cc1OC] | 6-chloro-7-(5,6-dimethoxy-2-(thiazol-2-yl)-1H-benzo[d]imidazol-1-yl)quinazo-line-2,4-dimaine |

TABLE 2-continued
| # | Structure | Name |
|---|---|---|
| 24 | 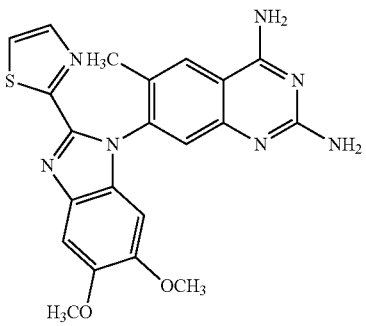 [SMILES: COc1cc2nc(-c3nccs3)n(-c3cc4nc(N)nc(N)c4cc3C)c2cc1OC] | 7-(5,6-dimethoxy-2-(thiazol-2-yl)-1H-benzo[d]-imidazol-1-yl)-6-methylquin-azoline-2,4-diamine |
| 25 | 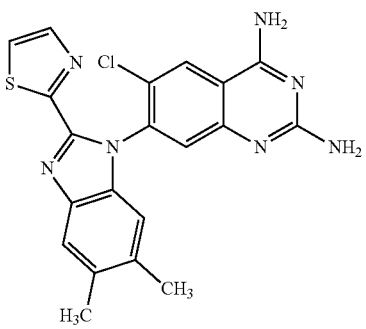 [SMILES: Cc1cc2nc(-c3nccs3)n(-c3cc4nc(N)nc(N)c4cc3Cl)c2cc1C] | 6-chloro-7-(5,6-dimethyl-2-(thiazol-2-yl)-1H-benzo[d]imidazol-1-yl)quinazoline-2,4-diamine |
| 26 | 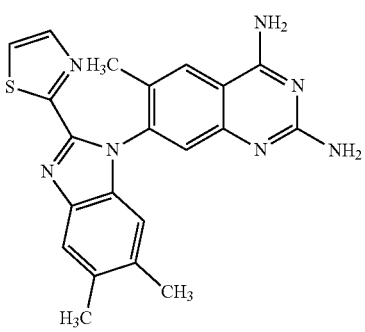 [SMILES: Cc1cc2nc(-c3nccs3)n(-c3cc4nc(N)nc(N)c4cc3C)c2cc1C] | 7-(5,6-dimethyl-2-(thiazol-2-yl)-1H-benzo[d]-imidazol-1-yl)-6-methylquin-azoline-2,4-diamine |
| 27 | 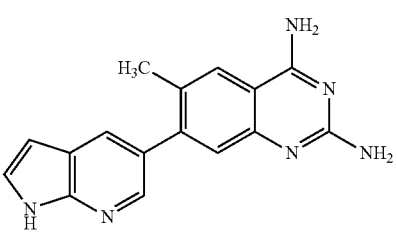 [SMILES: Cc1cc2c(N)nc(N)nc2cc1-c1cnc2[nH]ccc2c1] | 6-methyl-7-(1H-pyrrolo[2,3-b]pyridin-5-yl)quin-azoline-2,4-diamine |
| 28 | 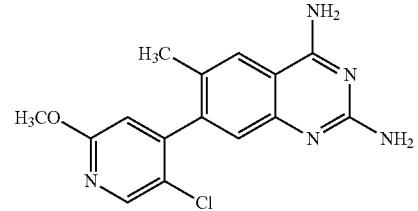 [SMILES: COc1cc(-c2cc3nc(N)nc(N)c3cc2C)c(Cl)cn1] | 7-(5-chloro-2-methoxypyridin-4-yl)-6-methylquin-azoline-2,4-diamine |

TABLE 2-continued

| # | Structure | Name |
|---|---|---|
| 29 | 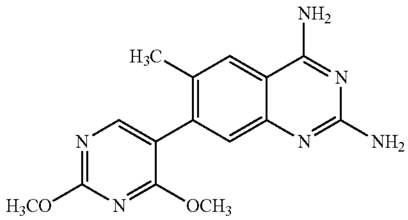 [SMILES: COc1ncc(-c2cc3nc(N)nc(N)c3cc2C)c(OC)n1] | 7-(2,4-dimethoxypyrimidin-5-yl)-6-methylquinazoline-2,4-diamine |
| 30 | 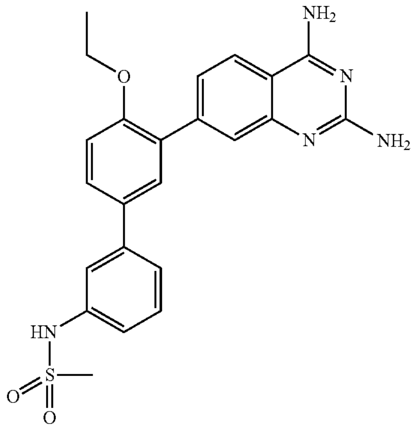 [SMILES: CCOc1ccc(-c2cccc(NS(C)(=O)=O)c2)cc1-c1ccc2c(N)nc(N)nc2c1] | N-(3'-(2,4-diaminoquinoazlin-7-yl)-4'-ethoxybiphenyl-3-yl)methanesulfonamide |
| 31 | 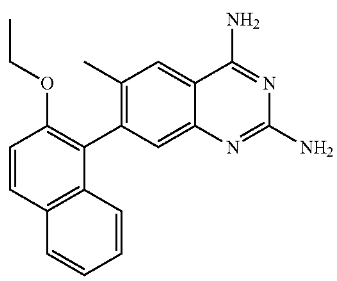 [SMILES: CCOc1ccc2ccccc2c1-c1cc2nc(N)nc(N)c2cc1C] | 7-(2-ethoxynaphthalen-1-yl)-6-methylquinazoline-2,4-diamine |
| 32 | 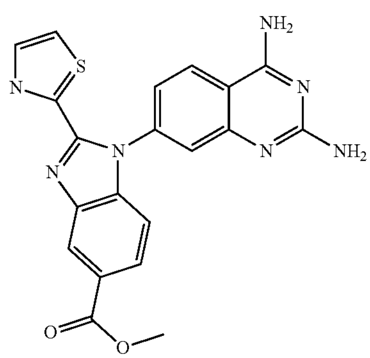 | methyl 1-(2,4-diaminoquinazolin-7-yl)-2-(thiazol-2-yl)-1H-benzo[d]imidazole-5-carboxylate |
| 33 | 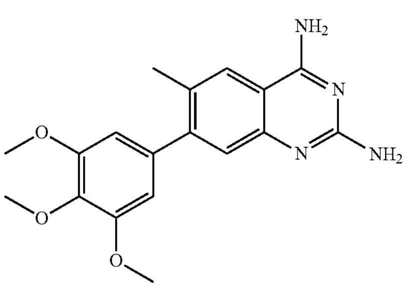 [SMILES: COc1cc(-c2cc3nc(N)nc(N)c3cc2C)cc(OC)c1OC] | 6-methyl-7-(3,4,5-trimethoxyphenyl) quinazoline-2,4-diamine |

TABLE 2-continued

| # | Structure | Name |
|---|---|---|
| 34 | 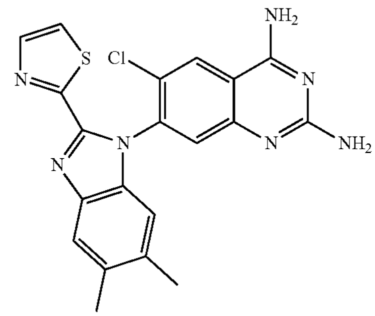 [SMILES: Cc1cc2nc(-c3nccs3)n(-c3cc4nc(N)nc(N)c4cc3Cl)c2cc1C] | 6-chloro-7-(5,6-dimethyl-2-(thiazol-2-yl)-1H-benzo[d]imidazol-1-yl)quinazoline-2,4-diamine |
| 35 | 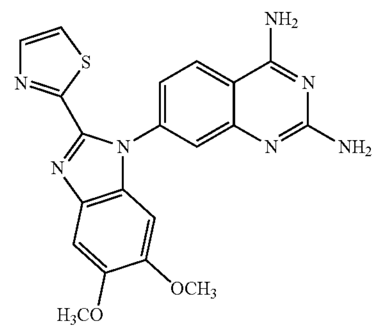 [SMILES: COc1cc2nc(-c3nccs3)n(-c3ccc4c(N)nc(N)nc4c3)c2cc1OC] | 7-(5,6-dimethoxy-2-thiazol-2-yl)-1H-benzo[d]imidazol-1-yl)quinazoline-2,4-diamine |
| 36 | 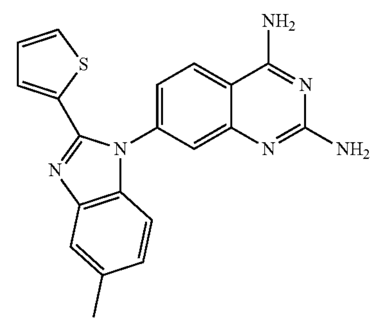 [SMILES: Cc1ccc2c(c1)nc(-c1cccs1)n2-c1ccc2c(N)nc(N)nc2c1] | 7-(5-methyl-2-thiophen-2-yl)-1H-benzo[d]imidazol-1-yl)quinazoline-2,4-diamine |
| 37 | 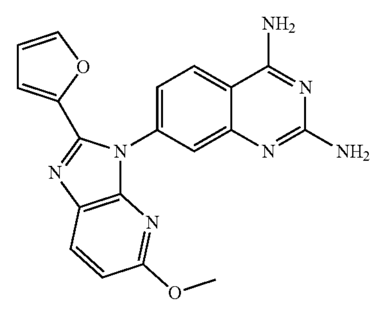 [SMILES: COc1ccc2nc(-c3ccco3)n(-c3ccc4c(N)nc(N)nc4c3)c2n1] | 7-(2-furan-2-yl)-5-methoxy-3H-imidazol[4,5-b]pyridine-3-yl)quinazoline-2,4-diamine |
| 38 | 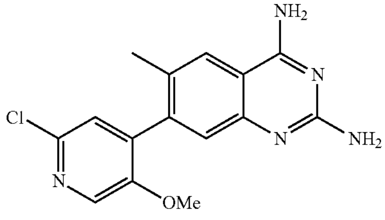 [SMILES: COc1cnc(Cl)cc1-c1cc2nc(N)nc(N)c2cc1C] | 7-(2-chloro-5-methyloxypyridin-4-yl)-6-methylquinazoline-2,4-diamine |

TABLE 2-continued

| # | Structure | Name |
|---|---|---|
| 39 | 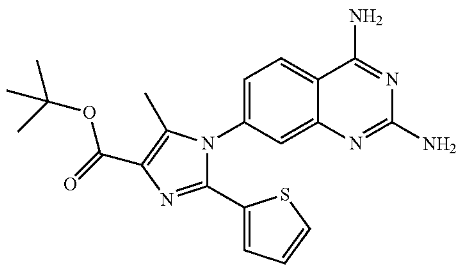 [SMILES: Cc1c(C(=O)OC(C)(C)C)nc(-c2cccs2)n1-c1ccc2c(N)nc(N)nc2c1] | tert-butyl 1-(2,4-diaminoquinazolin-7-yl)-5-methyl-2-thiophen-2-yl)-1H-imidazole-4-carboxylate |
| 40 | 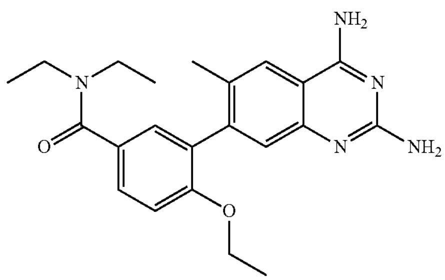 [SMILES: CCOc1ccc(C(=O)N(CC)CC)cc1-c1cc2nc(N)nc(N)c2cc1C] | 3-(2,4-diamino-6-methylquinazolin-7-yl)-4-ethoxy-N,N-diethylbenzamide |
| 41 | 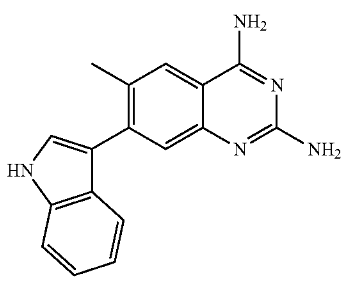 [SMILES: Cc1cc2c(N)nc(N)nc2cc1-c1c[nH]c2ccccc12] | 7-(1H-indol-3-yl)-6-methylquinazoline-2,4-diamine |

Determination of Anti-Bacterial Efficacy

Antibacterial Activity Assays

Antibacterial activity as measured by the minimal inhibitory concentrations (MIC) and minimal bactericidal concentrations of compounds are well known (see., e.g., National Committee for Clinical Laboratory Standards 2000 Performance standards for antimicrobial disk susceptibility tests: approved standard, 7$^{th}$ ed. M2-A7, vol. 20, no. 1, Committee for Clinical Laboratory Standards, Wayne, Pa.)

In vitro testing for antibacterial activity may be accomplished through use of a whole-cell bacterial growth inhibition assay. For example, an agar dilution assay identifies a substance that inhibits bacterial growth. Microtiter plates are prepared with serial dilutions of the test compound, adding to the preparation a given amount of growth substrate, and providing a preparation of bacteria. Inhibition of bacterial growth is determined, for example, by observing changes in optical densities of the bacterial cultures. Inhibition of bacterial growth is determined, for example, by comparing (in the presence and absence of a test compound) the rate of growth or the absolute growth of bacterial cells. Inhibition includes a reduction of one of the above measurements by at least 20%.

The compounds of the present invention are active against a wide range of bacteria. In some embodiments, the bacteria are Gram-positive bacteria including methicillin-susceptible and methicillin-resistant Staphylococci (including *Staphylococcus aureus, Staphylococcus epidermidis, Staphylococcus haemolyticus, Staphylococcus hominis, Staphylococcus saprophyticus*, and co-agulase-negative Staphylococci), glycopeptide intermediary-susceptible *Staphylococcus aureus* (GISA), penicillin-susceptible and penicillin-resistant Streptococci (including *Streptococcus pneumoniae, Streptococcus pyogenes, Streptococcus agalactiae, Streptococcus avium, Streptococcus bovis, Streptococcus lactis, Streptococcus sangius* and Streptococci Group C, Streptococci Group G and viridans Streptococci), enterococci (including vancomycin-susceptible and vancomycin-resistant strains such as *Enterococcus faecalis* and *Enterococcus faecium*), *Bacillus anthracis, Clostridium difficile, Clostridium clostridiiforme, Clostridium innocuum, Clostridium perfringens, Clostridium ramosum, Haemophilus influenzae, Listeria monocytogenes, Corynebacterium jeikeium, Bifidobacterium* spp., *Eubacterium aerqfaciens, Eubacterium lentum, lactobacillus acidophilus, Lactobacillus casei, Lactobacillus plantarum, Lactococcus* spp., *Leuconostoc* spp., *Pediococcus, Peptostreptococcus anaerobius, Peptostreptococcus asaccarolyticus, Peptostreptococcus magnus, Peptostreptococcus micros, Peptostreptococcus prevotii, Peptostreptococcus productus, Propionibacterium acnes*, and *Actinomyces* spp. In some embodiments, the Gram-positive bacterium is *Staphylococcus aureus*.

TABLE 3

Enzymatic and Antibacterial Activity of Compounds 1-41

| | MIC in μg/ml | | DHFR Ki (nM) | |
|---|---|---|---|---|
| Compound # | S. aureus | S. aureus in 20% serum | human DHFR | S. aureus DHFR |
| 1 | 2 | 4 | 1138 | 2.7 |
| 2 | 8 | 8 | 3922 | 15.3 |
| 3 | 4 | 8 | 345 | 4 |
| 4 | 4 | 2 | 702 | 2.7 |
| 5 | 1 | 1 | 138 | 0.89 |
| 6 | 4 | 8 | 323 | 4.4 |
| 7 | 0.5 | 1 | 26.3 | 0.48 |
| 8 | 1 | 1 | 27.5 | 0.66 |
| 9 | 0.25 | 1 | 245 | 0.61 |
| 10 | 8 | 2 | 53.6 | 0.51 |
| 11 | 1 | 2 | 55 | 1.2 |
| 12 | 1 | 1 | 44 | 0.65 |
| 13 | 0.5 | 2 | 44 | 0.5 |
| 14 | 4 | 4 | 263 | 1.6 |
| 15 | ≤0.5 | 1 | 1164 | 0.14 |
| 16 | ≤0.125 | 0.25 | 572 | 0.022 |
| 17 | ≤0.125 | 0.25 | 943 | 0.007 |
| 18 | ≤0.125 | 0.5 | 1026 | 0.005 |
| 19 | 1 | 4 | 1086 | 0.6 |
| 20 | 0.5 | 4 | 586 | 0.12 |
| 21 | ≤0.125 | 0.25 | 663 | 0.012 |
| 22 | ≤0.125 | ≤0.125 | 93.5 | 0.002 |
| 23 | ≤0.125 | 0.5 | 320 | 0.011 |
| 24 | ≤0.5 | ≤0.5 | 170 | 0.019 |
| 25 | ≤0.125 | 1 | 7.6 | 0.011 |
| 26 | ≤0.125 | ≤0.125 | 2.9 | 0.03 |
| 27 | 4 | 4 | 235 | 2.6 |
| 28 | 0.5 | 1 | 56 | 0.72 |
| 29 | 0.5 | 0.5 | 54.7 | 0.4 |
| 30 | ≤0.5 | 2 | 5.8 | 0.02 |
| 31 | ≤0.125 | 0.5 | 4.5 | 0.026 |
| 32 | 0.25 | 2 | 53.1 | 0.021 |
| 33 | ≤0.5 | 1 | 47.1 | 0.91 |
| 34 | ≤0.125 | 2 | 8.8 | 0.016 |
| 35 | 0.25 | 0.25 | 854 | 0.16 |
| 36 | 1 | 1 | 314 | 0.005 |
| 37 | 0.25 | 0.5 | 797 | 0.039 |
| 38 | 1 | 1 | 52.4 | 1.4 |
| 39 | 1 | 2 | 1913 | 0.2 |
| 40 | 0.25 | 0.25 | 34 | 0.025 |
| 41 | 0.25 | 0.5 | 50.5 | 0.11 |

Although the disclosure has been described with reference to the above examples, it will be understood that modifications and variations are encompassed within the spirit and scope of the disclosure. Accordingly, the disclosure is limited only by the following claims.

The invention claimed is:

1. A compound having the structure

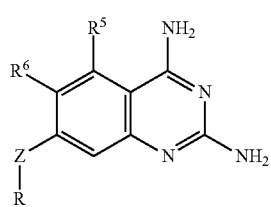

(Formula I)

wherein

Z is a seven to 10-membered heteroaryl ring comprising 0-4 heteroatoms independently selected from the group consisting of N, O, and S;

when two rings comprise the seven to 10-membered heteroaryl ring, the two rings are heteroaromatic;

R represents one or more moieties independently selected from the group consisting of H, halo, lower alkyl, lower alkoxy, $CF_3$, amino, CN, $CO_2CH_3$, optionally-substituted aryl, and optionally-substituted heterocyclyl;

$R^5$ is selected from the group consisting of H, halo, lower alkyl, and lower alkoxy;

$R^6$ is selected from the group consisting of H, halo, lower alkyl, lower alkoxy, $CF_3$, 5-membered heteroarylmethylene, and amino; and pharmaceutically acceptable salts and solvates thereof.

2. The compound of claim 1, wherein Z is selected from the group consisting of optionally-substituted isoquinoline, benzofuran, benzothiophene, indole, pyrrolopyridine, imidazopyridine, indazole benzimidazole, benzothiazole, quinoline, and benzotriazole.

3. The compound of claim 2, wherein Z is optionally-substituted benzimidazole.

4. The compound of claim 1, wherein R is selected from the group consisting of halo, optionally-substituted lower alkyl, lower alkoxy, and heterocyclyl.

5. The compound of claim 1, wherein R is selected from the group consisting of Me, Et, i-Pr, Cl, F, MeO, cyano, and $CF_3$.

6. The compound of claim 1, wherein R is an optionally-substituted heteroaryl group.

7. The compound of claim 1, wherein $R^5$ and $R^6$ are independently selected from the group consisting of F, Cl, lower alkyl, OMe, $CF_3$, $NMe_2$, and imidazolylmethyl.

8. The compound of claim 1, where the compound is

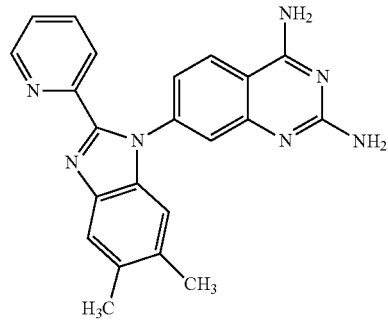 [SMILES: Cc1cc2nc(-c3ccccn3)n(-c3ccc4c(N)nc(N)nc4c3)c2cc1C]

7-(5,6-dimethyl-2-(pyridin-2-yl)-1H-benzo[d]-imidazol-1-yl)quinazoline-2,4-diamine.

9. The compound of claim 1, where the compound is

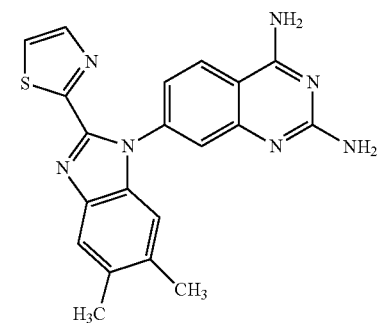 [SMILES: Cc1cc2nc(-c3nccs3)n(-c3ccc4c(N)nc(N)nc4c3)c2cc1C]

7-[5,6-dimethyl-2-(thiazol-2-yl)-1H-benzo[d]-imidazol-1-yl]quinazoline-2,4-diamine.

10. The compound of claim 1, where the compound is

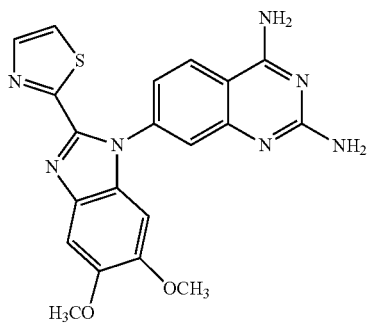 [SMILES: COc1cc2nc(-c3nccs3)n(-c3ccc4c(N)nc(N)nc4c3)c2cc1OC]

7-(5,6-dimethoxy-2-(thiazol-2-yl)-1H-benzo[d]imidazo-1-yl)quinazoline-2,4-diamine.

11. The compound of claim 1, where the compound is

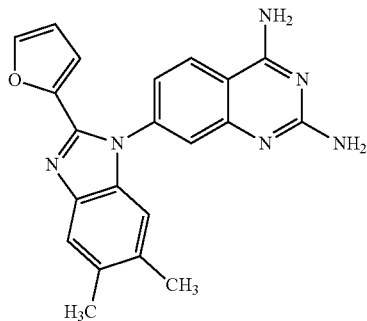 [SMILES: Cc1cc2nc(-c3ccco3)n(-c3ccc4c(N)nc(N)nc4c3)c2cc1C]

7-(2-(furan-2-yl)-5,6-dimethoxy-1H-benzo[d]-imidazol-1-yl)quinazoline-2,4-diamine.

12. The compound of claim 1, where the compound is

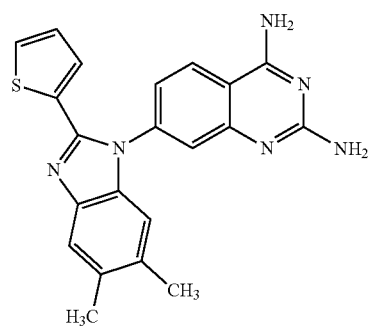

7-(5,6-dimethyl-2-(thiophen-2-yl)-1H-benzo[d]-imidazol-1-yl)quinazoline-2,4-diamine.

13. The compound of claim 1, where the seven to 10-membered heteroaryl ring is an eight to 10-membered heteroaryl ring.

14. A pharmaceutical composition comprising a compound of claim 1 and a pharmaceutically acceptable diluent or carrier.

15. A method of impeding growth of a bacterium by exposing the bacterium to a compound of claim 1.

* * * * *